United States Patent
Weaver et al.

(10) Patent No.: US 9,786,440 B2
(45) Date of Patent: Oct. 10, 2017

(54) ANODE FOR USE IN A HIGH VOLTAGE ELECTROLYTIC CAPACITOR

(71) Applicant: AVX Corporation, Fountain Inn, SC (US)

(72) Inventors: Mitchell D. Weaver, Simpsonville, SC (US); Lotfi Djebara, Paris (FR); Radek Matousek, Trebova (CZ)

(73) Assignee: AVX Corporation, Fountain Inn, SC (US)

( * ) Notice: Subject to any disclaimer, the term of this patent is extended or adjusted under 35 U.S.C. 154(b) by 111 days.

(21) Appl. No.: 14/572,939

(22) Filed: Dec. 17, 2014

(65) Prior Publication Data
US 2016/0181020 A1    Jun. 23, 2016

(51) Int. Cl.
| | |
|---|---|
| H01G 9/042 | (2006.01) |
| H01G 9/052 | (2006.01) |
| H01G 9/145 | (2006.01) |
| H01G 9/15 | (2006.01) |
| H01G 9/02 | (2006.01) |
| H01G 2/10 | (2006.01) |
| A61N 1/39 | (2006.01) |

(52) U.S. Cl.
CPC ......... *H01G 9/0525* (2013.01); *A61N 1/3956* (2013.01); *A61N 1/3975* (2013.01); *H01G 2/103* (2013.01); *H01G 9/02* (2013.01); *H01G 9/042* (2013.01); *H01G 9/145* (2013.01); *H01G 9/15* (2013.01)

(58) Field of Classification Search
CPC ......... H01G 9/04; H01G 9/145; H01G 9/035; H01G 9/045; H01G 9/042; H01G 9/028
See application file for complete search history.

(56) References Cited

U.S. PATENT DOCUMENTS

| | | |
|---|---|---|
| 5,111,327 A | 5/1992 | Blohm et al. |
| 5,369,547 A | 11/1994 | Evans |
| 5,486,977 A | 1/1996 | Hasegawa |
| 5,667,536 A | 9/1997 | Hasegawa |
| 5,716,511 A | 2/1998 | Melody et al. |
| 5,808,857 A | 9/1998 | Stevens |
| 5,922,215 A | 7/1999 | Pless et al. |
| 5,930,109 A | 7/1999 | Fishler |
| 5,968,210 A | 10/1999 | Strange et al. |
| 5,983,472 A | 11/1999 | Faygram et al. |
| 6,094,339 A | 7/2000 | Evans |

(Continued)

OTHER PUBLICATIONS

Related U.S. Patent Application Form.

*Primary Examiner* — Nguyen Ha
(74) *Attorney, Agent, or Firm* — Dority & Manning, P.A.

(57) ABSTRACT

An anode for use in a high voltage electrolytic capacitor is provided. The anode contains a sintered porous pellet and a leadwire extending therefrom in a longitudinal direction. The pellet is multi-layered to the extent that it contains at least a first layer positioned adjacent to a second layer, both of which extend along the length of the anode. The anode leadwire is embedded within the first layer. For this reason, the first layer has a thickness greater than that of the leadwire. Nevertheless, the use of a separate and distinct second layer adjacent to the first layer can allow each of the layers to be independently pressed using a multi-sided compaction device so that the properties of the anode are not significantly impacted by the presence of the relatively large anode leadwire.

18 Claims, 4 Drawing Sheets

(56) References Cited

U.S. PATENT DOCUMENTS

| | | |
|---|---|---|
| 6,139,593 A | 10/2000 | Kono |
| 6,162,345 A | 12/2000 | Kinard et al. |
| 6,197,252 B1 | 3/2001 | Bishop et al. |
| 6,231,993 B1 | 5/2001 | Stephenson et al. |
| 6,238,810 B1 | 5/2001 | Strange et al. |
| 6,246,569 B1 | 6/2001 | Strange et al. |
| 6,249,423 B1 | 6/2001 | O'Phelan et al. |
| 6,261,434 B1 | 7/2001 | Melody et al. |
| 6,267,861 B1 | 7/2001 | Kinard et al. |
| 6,346,185 B1 | 2/2002 | Kinard et al. |
| 6,377,442 B1 | 4/2002 | Strange et al. |
| 6,421,226 B1 | 7/2002 | O'Phelan et al. |
| 6,426,864 B1 | 7/2002 | O'Phelan et al. |
| 6,556,863 B1 | 4/2003 | O'Phelan et al. |
| 6,594,140 B1 | 7/2003 | Evans et al. |
| 6,635,729 B1 | 10/2003 | Groenendaal et al. |
| 6,659,283 B1 | 12/2003 | Muffoletto et al. |
| 6,775,127 B2 * | 8/2004 | Yoshida ............... H01G 9/052 361/528 |
| 6,786,951 B2 | 9/2004 | He et al. |
| 6,802,951 B2 | 10/2004 | Hossick-Schott |
| 6,802,954 B1 | 10/2004 | Hemphill et al. |
| 6,815,306 B1 | 11/2004 | Strange et al. |
| 6,858,126 B1 | 2/2005 | Hemphill et al. |
| 6,965,510 B1 | 11/2005 | Liu et al. |
| 6,987,663 B2 | 1/2006 | Merker et al. |
| 7,043,300 B2 | 5/2006 | O'Phelan et al. |
| 7,090,762 B2 | 8/2006 | Tripp et al. |
| 7,099,143 B1 * | 8/2006 | Fife ..................... H01G 9/035 361/503 |
| 7,150,767 B1 | 12/2006 | Schneider et al. |
| 7,150,776 B2 | 12/2006 | Shekhter et al. |
| 7,196,899 B1 | 3/2007 | Feger et al. |
| 7,207,103 B2 | 4/2007 | Poltorak |
| 7,214,279 B2 | 5/2007 | Fischer et al. |
| 7,244,279 B2 | 7/2007 | Seitz et al. |
| 7,248,462 B2 | 7/2007 | Melody et al. |
| 7,271,994 B2 | 9/2007 | Stemen et al. |
| 7,286,336 B2 | 10/2007 | Liu et al. |
| 7,342,774 B2 | 3/2008 | Hossick-Schott et al. |
| 7,385,802 B1 | 6/2008 | Ribble et al. |
| 7,445,646 B1 | 11/2008 | Strange et al. |
| 7,483,260 B2 | 1/2009 | Ziarniak et al. |
| 7,531,010 B1 | 5/2009 | Feger et al. |
| 7,544,218 B2 | 6/2009 | Norton et al. |
| 7,558,051 B2 | 7/2009 | O'Phelan et al. |
| 7,678,259 B2 | 3/2010 | Meloday et al. |
| 7,684,171 B2 | 3/2010 | Rorvick et al. |
| 7,715,174 B1 | 5/2010 | Beauvais et al. |
| 7,727,372 B2 | 6/2010 | Liu et al. |
| 7,731,893 B2 | 6/2010 | Freeman et al. |
| 7,837,743 B2 | 11/2010 | Gaffney et al. |
| 7,846,217 B2 | 12/2010 | Poplett |
| 7,879,217 B2 | 2/2011 | Goad et al. |
| 8,023,250 B2 | 9/2011 | Ning et al. |
| 8,038,866 B2 | 10/2011 | Jiang et al. |
| 8,114,340 B2 | 2/2012 | McCracken et al. |
| 8,206,600 B2 | 6/2012 | Ribble |
| 8,257,463 B2 | 9/2012 | Fife et al. |
| 8,279,583 B2 * | 10/2012 | Zednicek ............... H01G 9/052 361/528 |
| 8,279,585 B2 | 10/2012 | Dreissig et al. |
| 8,298,478 B2 * | 10/2012 | Hintz ..................... A61N 1/05 361/508 |
| 8,313,621 B2 | 11/2012 | Goad et al. |
| 8,477,479 B2 * | 7/2013 | Pease ..................... H01G 9/008 29/25.03 |
| 8,514,547 B2 | 8/2013 | Galvagni et al. |
| 8,619,408 B2 | 12/2013 | Sherwood et al. |
| 8,687,347 B2 | 4/2014 | Bates et al. |
| 2004/0147960 A1 * | 7/2004 | O'Phelan ............... A61N 1/375 607/1 |
| 2006/0023400 A1 * | 2/2006 | Sherwood ............ H01G 9/0032 361/503 |
| 2006/0091020 A1 | 5/2006 | Hossick-Schott et al. |
| 2007/0025063 A1 * | 2/2007 | Viste ..................... C25D 11/02 361/505 |
| 2008/0232032 A1 | 9/2008 | Jones et al. |
| 2010/0318140 A1 | 12/2010 | Hintz et al. |
| 2013/0141841 A1 | 6/2013 | Dreissig et al. |
| 2013/0155580 A1 | 6/2013 | Karnik et al. |
| 2014/0218843 A1 | 8/2014 | Evans |
| 2014/0268497 A1 | 9/2014 | Weaver et al. |
| 2014/0268498 A1 | 9/2014 | Weaver |
| 2014/0268499 A1 | 9/2014 | O'Phelan et al. |

* cited by examiner

ANODE FOR USE IN A HIGH VOLTAGE ELECTROLYTIC CAPACITOR

BACKGROUND OF THE INVENTION

High voltage electrolytic capacitors are often employed in implantable medical devices. These capacitors are required to have a high energy density because it is desirable to minimize the overall size of the implanted device. This is particularly true of an implantable cardioverter defibrillator ("ICD"), also referred to as an implantable defibrillator, because the high voltage capacitors used to deliver the defibrillation pulse can occupy as much as one third of the ICD volume. ICDs typically use two to four electrolytic capacitors in series to achieve the desired high voltage for shock delivery. Typically, metal foils (e.g., aluminum foil) are used in the electrolytic capacitor due to their small size. Because the electrostatic capacitance of the capacitor is proportional to its electrode area, the surface of the metallic foil may be, prior to the formation of the dielectric film, roughened or subjected to a chemical conversion to increase its effective area. This step of roughening the surface of the metallic foil is called etching. Etching is normally carried out either by the method (chemical etching) of conducting immersion into a solution of hydrochloric acid or by the method (electrochemical etching) of carrying out electrolysis in an aqueous solution of hydrochloric acid. The capacitance of the electrolytic capacitor is determined by the extent of roughing (the surface area) of the anode foil and the thickness and the dielectric constant of the oxide film.

Due to the limited surface area that may be provided by etching metallic foils, attempts have also been made to employ porous sintered pellets in wet electrolytic capacitors—i.e., "wet tantalum" capacitors. The anode of a typical wet electrolytic capacitor includes a porous anode body, with an anode leadwire extending beyond the anode body. The anode can be formed by first pressing a tantalum powder into a pellet that is then sintered to create fused connections between individual powder particles. Unfortunately, when forming such anodes for high voltage medical applications, problems are often experienced. Namely, in such anodes, it is often difficult to create a sufficient number of contacts between the anode leadwire and the tantalum powder particles, which can result in an increase in equivalent series resistance (ESR).

As such, a need currently exists for an improved anode for use in high voltage capacitor, such as those employed in implantable medical devices.

SUMMARY OF THE INVENTION

In accordance with one embodiment of the present invention, an anode for use in an electrolytic capacitor is disclosed. The anode comprises a sintered porous pellet that contains a first layer positioned adjacent to a second layer, wherein the first layer has a thickness greater than that of the second layer. A leadwire is embedded in the first layer of the pellet that extends therefrom in a longitudinal direction and has a thickness of about 0.1 millimeter or more. A dielectric layer is also formed on the pellet.

In accordance with another embodiment of the present invention, a wet electrolytic capacitor is disclosed that comprises an anode, a cathode that comprises a metal substrate coated with a conductive coating, and a fluidic working electrolyte in communication with the anode and the cathode. The anode comprises a sintered porous pellet and a dielectric layer formed on the pellet. The pellet contains a first layer positioned adjacent to a second layer, wherein the first layer has a thickness greater than that of the second layer. A leadwire is embedded in the first layer of the pellet that extends therefrom in a longitudinal direction and has a thickness of about 0.1 millimeter or more.

In accordance with yet another embodiment of the present invention, a method for forming an anode for use in an electrolytic capacitor is disclosed. The method comprises loading a first valve metal powder into a first die cavity of a press mold, wherein an anode leadwire is embedded within the first valve metal powder; loading a second valve metal powder to a second die cavity of the press mold; forming a pellet by compressing the first valve metal powder with a first punch and compressing the second valve metal powder with a second punch; sintering the pellet; and anodically oxidizing the sintered pellet to form a dielectric layer.

Other features and aspects of the present invention are set forth in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIG. 5 is a schematic illustration of one embodiment of the present invention for pressing powders into a multi-layered pellet, in which

Figure 1:
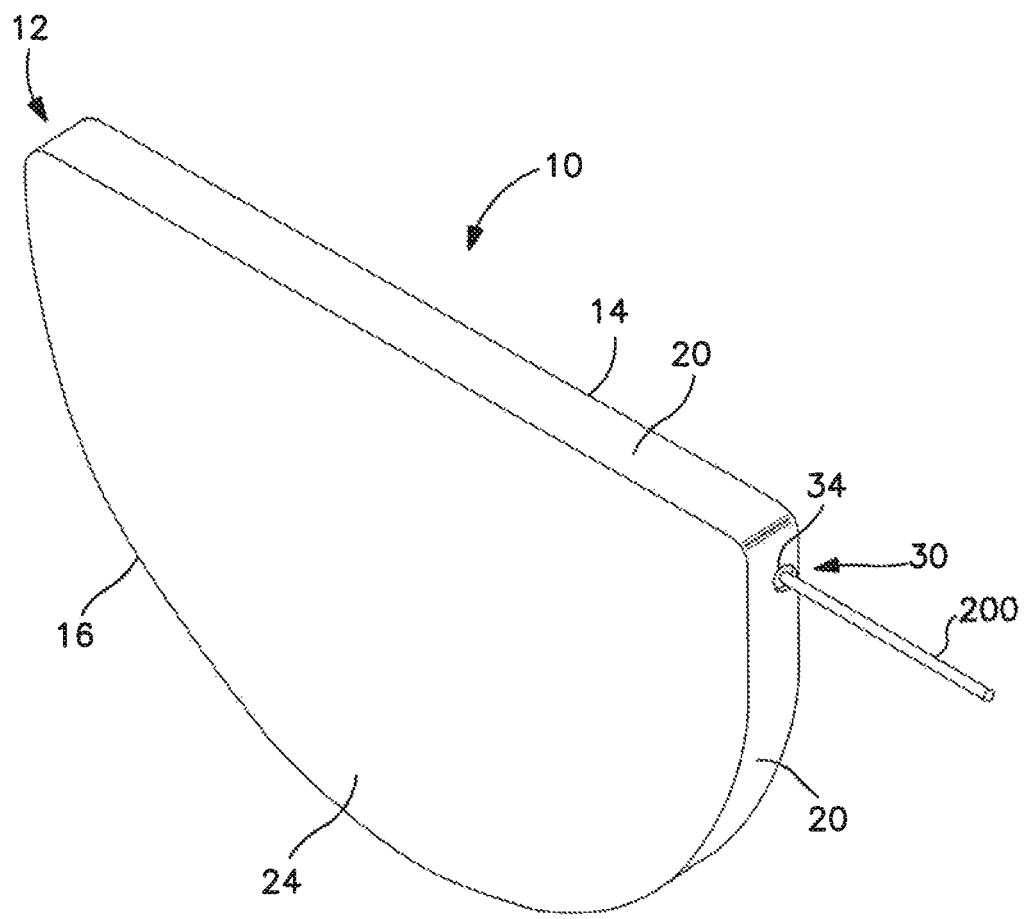
FIG. 1 is a perspective view of one embodiment of the wet electrolytic capacitor of the present invention.

Repeat use of references characters in the present specification and drawings is intended to represent same or analogous features or elements of the invention.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention, which broader aspects are embodied in the exemplary construction.

Generally speaking, the present invention is directed to an anode for use in a high voltage electrolytic capacitor. The anode contains a sintered porous pellet and a leadwire extending therefrom in a longitudinal direction. To help minimize equivalence series resistance ("ESR"), the leadwire may be relatively thick in nature. For example, the leadwire may have a thickness (e.g., diameter) of about 0.1 millimeters or more, in some embodiments about 0.2 millimeters or more, and in some embodiments, from about 0.3 to about 3 millimeters. The pellet is also multi-layered to the extent that it contains at least a first layer positioned adjacent to a second layer, both of which extend along the length of the anode. Notably, the anode leadwire is embedded within the first layer. For this reason, the first layer has a thickness greater than that of the leadwire. The ratio of the thickness of the first layer to the thickness of the leadwire may, for instance, be from about 1.0 to about 8.0, in some embodiments from about 1.5 to about 5.0, and in some embodiments, from about 2.0 to about 4.0. In certain embodiments, for instance, the thickness of the first layer may range from about 0.2 to about 10 millimeters, in some embodiments from about 0.5 to about 5 millimeters, and in some embodiments, from about 0.8 to about 4 millimeters.

Due to the relatively large thickness of the first layer, the present inventors have discovered that the leadwire can be readily embedded therein. Conventionally, it has been difficult to press such thick layers into pellets having consistently good properties. The present inventors have discovered, however, that the use of a separate and distinct second layer adjacent to the first layer can allow each of the layers to be independently pressed using a multi-sided compaction device so that the properties of the anode are not significantly impacted by the presence of the relatively large anode leadwire. The ratio of the thickness of the first layer to the thickness of the second layer may, for instance, range from about 1.0 to about 5.0, in some embodiments from about 1.1 to about 3.0, and in some embodiments, from about 1.2 to about 2.0. In certain embodiments, for instance, the thickness of the second layer may from about 0.1 to about 5 millimeters, in some embodiments, from about 0.4 to about 3 millimeters, and in some embodiments, from about 0.5 to about 2 millimeters.

Various embodiments of the present invention will now be described in more detail.

I. Anode

As noted above, the anode contains a sintered porous pellet. To improve electrical performance and volumetric efficiency, the anode is typically planar in nature in that its length is substantially greater than its thickness. For example, the ratio of the length of the anode to the thickness of the anode may be from about 5 to about 60, in some embodiments from about 6 to about 50, and in some embodiments from about 7 to about 40. The length of the anode may, for instance, range from about 1 to about 80 millimeters, in some embodiments from about 10 to about 60 millimeters, and in some embodiments, from about 20 to about 50 millimeters, while the thickness of the anode may from about 10 millimeters or less, in some embodiments, from about 0.5 to about 8 millimeters, and in some embodiments, from about 1 to about 6 millimeters.

Figure 2:
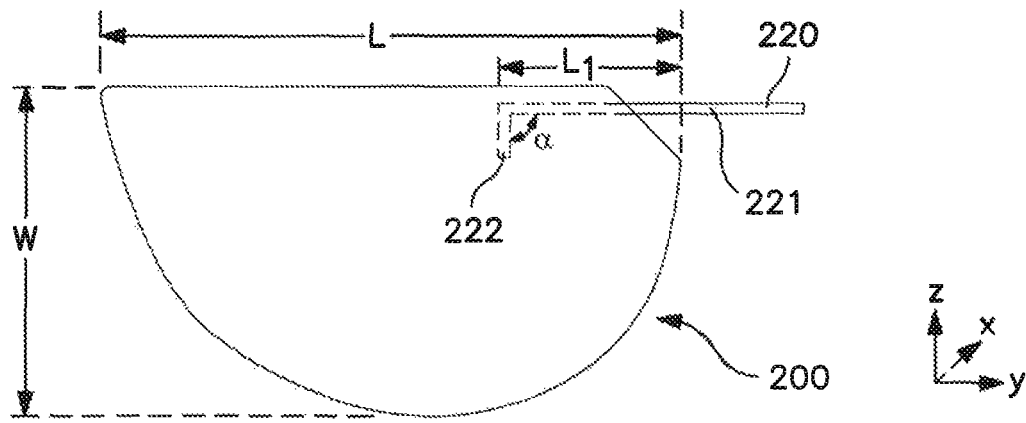
FIG. 2 is a top view of embodiment of an anode that may be employed in the capacitor of the present invention.
Figure 3:
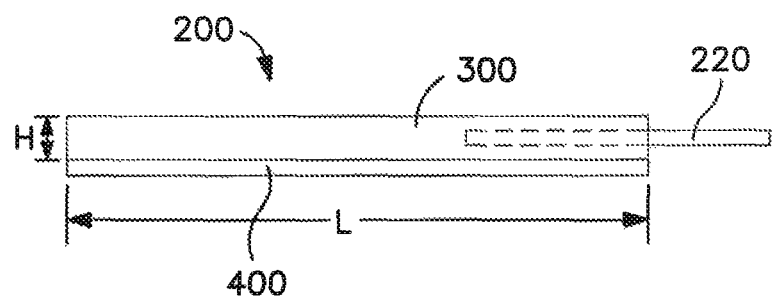
FIG. 3 is a frontal view of the anode of FIG. 2.

Referring to FIGS. 2-3, for example, one embodiment of a planar anode 200 is shown that has a thickness "H", width "W", and length "L." The thickness and length may be within the ranges noted above. The width "W" of the anode may likewise range from about 0.05 to about 40 millimeters, in some embodiments, from about 0.5 to about 25 millimeters, and in some embodiments, from about 2 to about 10 millimeters. Although shown as a "D-shape" in FIG. 2, it should also be understood that the anode may possess any other desired shape, such as square, rectangle, circle, oval, triangle, etc. Polygonal shapes having more than four (4) edges (e.g., hexagon, octagon, heptagon, pentagon, etc.) are particularly desired due to their relatively high surface area.

As shown in FIG. 3, the planar anode 200 contains a first layer 300 positioned adjacent to a second layer 400. The layers 300 and 400 extend in the longitudinal direction (-y direction), which in this embodiment, is also in the direction of the anode length "L." An anode leadwire 220 is embedded within the first layer 300 and may be formed from any conductive material, such as a valve metal compound (e.g., tantalum, niobium, niobium oxide, etc.). Due to the thin nature of the planar anode, it is sometimes desirable to control the manner in which the leadwire 220 is embedded within the first layer 300 to the extent that stresses applied during manufacturing will cause the wire to pull out of the anode. For example, in one embodiment, at least a portion of the wire within the anode is bent at an angle relative to the longitudinal axis of the wire. This "bend" reduces the ease to which the wire can be pulled out in the longitudinal direction after the anode is pressed and sintered.

Referring again to FIGS. 2-3, the leadwire 220 contains a first portion 221 that extends in the longitudinal direction ("y" direction) from the anode 200. Within the body of the anode, the wire 200 also contains a second portion 222 that is bent at an angle "α" relative to the first portion 221. The angle "α" is typically from about 40° to about 120°, in some embodiments from about 60° to about 110°, and in some embodiments, from about 80° to about 100° (e.g., about 90°). In addition to its geometric configuration, the extent to which the anode wire is inserted into the anode may also be controlled to help minimize the likelihood of withdrawal during manufacturing. That is, the wire is less likely to be pulled out of the anode the farther it is inserted. Of course, too great of a wire insertion can alter the uniformity of the press density, which can impact the resulting electrical performance of the anode. In this regard, the ratio of the length of the anode in which the wire is inserted to the entire length of the anode is typically from about 0.1 to about 0.6, and in some embodiments, from about 0.2 to about 0.5. In FIG. 2, for example, the length "$L_1$" represents the length of the anode 200 in which the anode wire 220 is inserted, while the length "L" represents the entire length of the anode 200. The length "$L_1$" may be from about 1 to about 40 millimeters, in some embodiments, from about 2 to about 20 millimeters, and in some embodiments, from about 5 to about 15 millimeters.

Regardless of the particular wire configuration, the first and second layers of the anode may be formed from a valve metal powder that contains a valve metal (i.e., metal that is capable of oxidation) or valve metal-based compound, such as tantalum, niobium, aluminum, hafnium, titanium, alloys thereof, oxides thereof, nitrides thereof, and so forth. For example, the valve metal powder may contain an electrically conductive oxide of niobium, such as niobium oxide having an atomic ratio of niobium to oxygen of 1:1.0±1.0, in some embodiments 1:1.0±0.3, in some embodiments 1:1.0±0.1, and in some embodiments, 1:1.0±0.05. The niobium oxide may be $NbO_{0.7}$, $NbO_{1.0}$, $NbO_{1.1}$, and $NbO_2$. Although not required, it is typically desired that the first and second layers are formed from the same type of powder.

A powder may be formed using any of a variety of processes known in the art, such as electron beam melting, reduction, etc. A tantalum powder, for instance, may be formed by reducing a tantalum salt (e.g., potassium fluorotantalate ($K_2TaF_7$), sodium fluorotantalate ($Na_2TaF_7$), tantalum pentachloride ($TaCl_5$), etc.) with an alkali reducing agent (e.g., sodium). In yet other embodiments, the powder may also be formed by reacting an oxide of a valve metal compound with a reducing agent that contains a metal having a relatively high oxidation state (e.g., magnesium). The valve metal oxide is typically a tantalum and/or niobium oxide capable of being reduced, such as $Ta_2O_x$ ($x \leq 5$) (e.g., $Ta_2O$) or $Nb_2O_x$ ($x \leq 5$) (e.g., $Nb_2O_5$). The reducing agent may be provided in a gaseous, liquid, or solid state, and may also be in the form of the metal, as well as alloys or salts thereof. In one embodiment, for instance, a halide salt (e.g., chloride, fluoride, etc.) may be employed. If desired, other components may also be added before, during, or after the reaction, such as dopants, alkali metals, etc. The reduction of the oxide is typically carried out at a temperature of from about 400° C. to about 1200° C., and in some embodiments, from about 600° C. to about 1000° C., for about 20 to about 300 minutes. Heating may be carried out in a reactor under an inert atmosphere (e.g., argon or nitrogen atmosphere) so that a molten bath is formed. Suitable reactors may include, for instance, vertical tube furnaces, rotary kilns, fluid bed furnaces, multiple hearth furnaces, self-propagation high-temperature synthesis reactors, etc. The reactor may be maintained under inert gas until that the mass in the reaction vessel is cooled to ambient temperature. Additional details of such a reduction reaction may be described in U.S. Patent Publication Nos. 2003/0110890 to He, et al. and 2004/0163491 to Shekhter, et al. After the reduction, the product may be cooled, crushed, and washed to remove excess impurities or reactants.

The resulting powder may be a free-flowing, finely divided powder that contains primary particles having any of a variety of shapes, such as a relatively flat shape (e.g., flakes) or three-dimensional shape (e.g., nodular or angular). When three-dimensional particles are employed, such particles typically have a relatively low "aspect ratio", which is the average diameter or width of the particles divided by the average thickness ("D/T"). For example, the aspect ratio of the particles may be about 4 or less, in some embodiments about 3 or less, and in some embodiments, from about 1 to about 2. The powder may also have a relatively high specific surface area, such as about 1 square meter per gram ("$m^2/g$") or more, in some embodiments about 2 $m^2/g$ or more, and in some embodiments, from about 4 to about 30 $m^2/g$. The term "specific surface area" generally refers to surface area as determined by the physical gas adsorption (B.E.T.) method of Bruanauer, Emmet, and Teller, Journal of American Chemical Society, Vol. 60, 1938, p. 309, with nitrogen as the adsorption gas. The test may be conducted with a MONOSORB® Specific Surface Area Analyzer available from QUANTACHROME Corporation, Syosset, N.Y., which measures the quantity of adsorbate nitrogen gas adsorbed on a solid surface by sensing the change in thermal conductivity of a flowing mixture of adsorbate and inert carrier gas (e.g., helium).

The primary particles of the powder may also have a median size (D50) of from about 5 to about 250 nanometers, and in some embodiments, from about 10 to about 100 nanometers, such as using a laser particle size distribution analyzer made by BECKMAN COULTER Corporation (e.g., LS-230), optionally after subjecting the particles to an ultrasonic wave vibration of 70 seconds. Due to its high surface area and low particle size, the powder may have a high specific charge, such as greater than about 5,000 microFarads*Volts per gram ("$\mu F^*V/g$"), in some embodiments from about 10,000 to about 80,000 $\mu F^*V/g$, and in some embodiments, from about 15,000 to about 45,000 $\mu F^*V/g$. As is known in the art, the specific charge may be determined by multiplying capacitance by the anodizing voltage employed, and then dividing this product by the weight of the anodized electrode body.

The powder (as well as the anode) may also have a relatively low alkali metal, carbon, and oxygen content. For example, the powder may have no more than about 50 ppm carbon or alkali metals, and in some embodiments, no more than about 10 ppm carbon or alkali metals. Likewise, the powder may have no more than about 0.15 ppm/$\mu$C/g oxygen, and in some embodiments, no more than about 0.10 ppm/$\mu$C/g oxygen. Oxygen content may be measured by LECO Oxygen Analyzer and includes oxygen in natural oxide on the tantalum surface and bulk oxygen in the tantalum particles. Bulk oxygen content is controlled by period of crystalline lattice of tantalum, which is increasing linearly with increasing oxygen content in tantalum until the solubility limit is achieved. This method was described in "Critical Oxygen Content In Porous Anodes Of Solid Tantalum Capacitors", Pozdeev-Freeman et al., Journal of Materials Science: Materials In Electronics 9, (1998) 309-311 wherein X-ray diffraction analysis (XRDA) was employed to measure period of crystalline lattice of tantalum. Oxygen in sintered tantalum anodes may be limited to thin natural surface oxide, while the bulk of tantalum is practically free of oxygen.

Certain additional components may also be included in the powder. For example, the powder may be optionally mixed with a binder and/or lubricant to ensure that the particles adequately adhere to each other when compacted or pressed to form the pellet. Suitable binders may include, for instance, poly(vinyl butyral); poly(vinyl acetate); poly(vinyl alcohol); poly(vinyl pyrollidone); cellulosic polymers, such as carboxymethylcellulose, methyl cellulose, ethyl cellulose, hydroxyethyl cellulose, and methylhydroxyethyl cellulose; atactic polypropylene, polyethylene; polyethylene glycol (e.g., Carbowax from Dow Chemical Co.); polystyrene, poly(butadiene/styrene); polyamides, polyimides, and polyacrylamides, high molecular weight polyethers; copolymers of ethylene oxide and propylene oxide; fluoropolymers, such as polytetrafluoroethylene, polyvinylidene fluoride, and fluoro-olefin copolymers; acrylic polymers, such as sodium polyacrylate, poly(lower alkyl acrylates), poly (lower alkyl methacrylates) and copolymers of lower alkyl acrylates and methacrylates; and fatty acids and waxes, such as stearic and other soapy fatty acids, vegetable wax, microwaxes (purified paraffins), etc. The binder may be dissolved and dispersed in a solvent. Exemplary solvents may include water, alcohols, and so forth. When utilized, the percentage of binders and/or lubricants may vary from about 0.1% to about 8% by weight of the total mass. It should be understood, however, that binders and/or lubricants are not necessarily required in the present invention.

Once formed, one or multiple powders may be compacted into to form a multi-layered anode as described above. Various types of compaction devices may be employed, such as a compaction press using multiple punches. Such press molds are available in several basic types, such as cam, toggle/knuckle and eccentric/crank presses with varying capabilities, such as single action, double action, floating die, movable platen, opposed ram, screw, impact, hot pressing, coining or sizing. Regardless of the type of device employed, a first powder is typically compacted around the leadwire to form a relatively thick first layer while a second powder is typically compacted to form a relatively thin second layer.

Figure 5A:
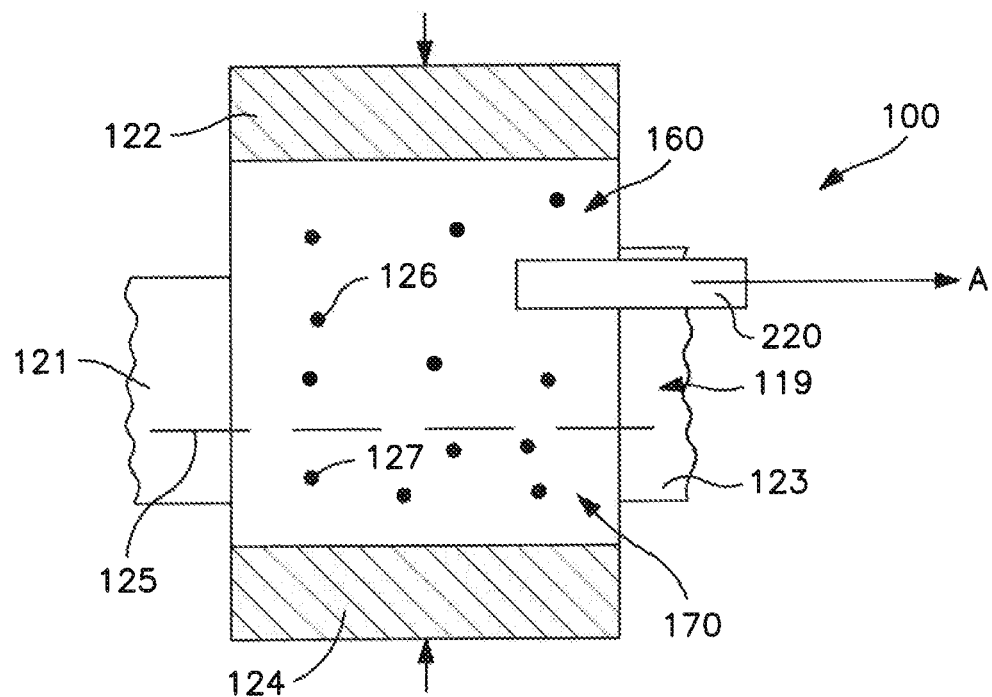
FIG. 5A illustrates the press mold prior to compaction and FIG. 5B illustrates the press mold after compaction.
Figure 5B:
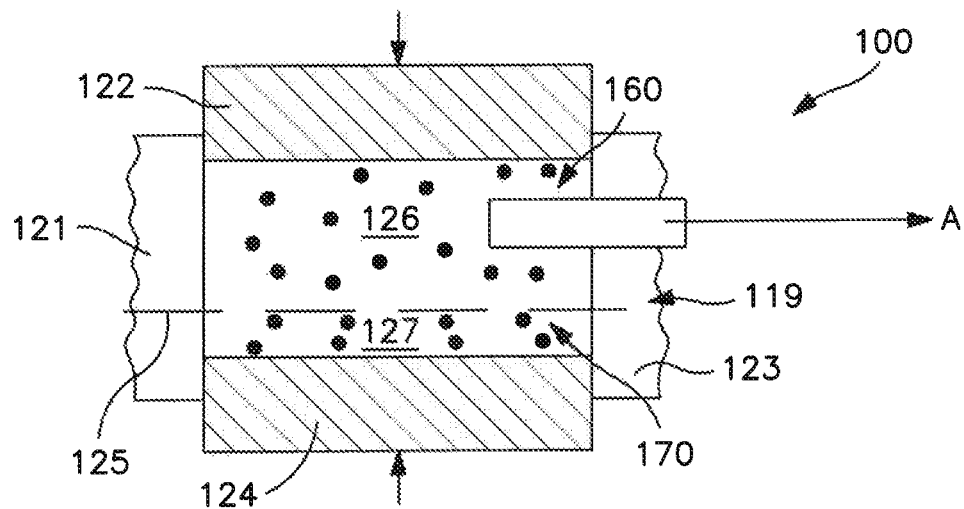

Referring to FIGS. 5A and 5B, for example, one embodiment of the present invention for compacting powders into a multi-layered anode using a press mold 100 will now be described in more detail. In this particular embodiment, the press mold 100 includes a die 119 having a first die portion 121 and a second die portion 123 separated by a removable partition 125. Of course, the die 119 may also be formed from a single part instead of multiple portions. Nevertheless, in FIGS. 5A and 5B, the first die portion 121 and the partition 125 define a first die cavity 160 for forming the first layer of the anode and the second die portion 123 and the partition 125 define a second die cavity 170 for forming the second layer. As shown in FIG. 5A, a certain quantity of a first valve metal powder 126 may be loaded into the first die cavity 160 and the leadwire 220 (e.g., tantalum wire) may be embedded therein. Similarly, a certain quantity of a second valve metal powder 127, which may be the same or different than the first powder 126, may be loaded into the second die cavity 170.

After filling, the partition 125 may be removed and the die cavities may be closed so that the powders 126 and 127 can be compressed by a first punch 122 and a second punch 124, respectively. The direction in which the compressive forces are exerted may provide improved properties to the resulting capacitor. For example, as illustrated by the directional arrows in FIG. 5B, the forces exerted by the punches are in a direction that is substantially "perpendicular" to a longitudinal axis "A" of the wire 220. That is, the force is typically exerted at an angle of from about 60° to about 120°, and preferably about 90° relative to the axis "A." Such a "perpendicular" pressing technique can force the particles into close contact with the wire 220 and create a strong wire-to-powder bond. In addition, the "perpendicular" pressing technique can also reduce the likelihood that the wire will be bent, thereby decreasing the likelihood of cracks or weak areas. On the other hand, "parallel" pressing techniques (i.e., force exerted by the punches are in a direction that is substantially parallel to the longitudinal axis "A") tend to bend the wire instead of allowing it to penetrate the powder.

Once pressed into the form of a multi-layered anode pellet, any binder/lubricant may be removed after pressing by heating the pellet under vacuum at a certain temperature (e.g., from about 150° C. to about 500° C.) for several minutes. Alternatively, the binder/lubricant may also be removed by contacting the pellet with an aqueous solution, such as described in U.S. Pat. No. 6,197,252 to Bishop, et al. Thereafter, the pellet is sintered to form a porous, integral mass. The pellet is typically sintered at a temperature of from about 800° C. to about 2000° C., in some embodiments from about 1200° C. to about 1800° C., and in some embodiments, from about 1500° C. to about 1700° C., for a time of from about 5 minutes to about 100 minutes, and in some embodiments, from about 8 minutes to about 15 minutes. This may occur in one or more steps. If desired, sintering may occur in an atmosphere that limits the transfer of oxygen atoms to the anode. For example, sintering may occur in a reducing atmosphere, such as in a vacuum, inert gas, hydrogen, etc. The reducing atmosphere may be at a pressure of from about 10 Torr to about 2000 Torr, in some embodiments from about 100 Torr to about 1000 Torr, and in some embodiments, from about 100 Torr to about 930 Torr. Mixtures of hydrogen and other gases (e.g., argon or nitrogen) may also be employed.

The anode also contains a dielectric layer formed over and/or within the pellet, such as through an anodic oxidation process. For example, a tantalum (Ta) anode may be anodized to tantalum pentoxide ($Ta_2O_5$). Typically, anodization is performed by initially applying a solution to the anode, such as by dipping anode into the electrolyte. Aqueous solvents (e.g., water) and/or non-aqueous solvents (e.g., ethylene glycol) may be employed. To enhance conductivity, a compound may be employed that is capable of dissociating in the solvent to form ions. Examples of such compounds include, for instance, acids, such as described below with respect to the electrolyte. For example, an acid (e.g., phosphoric acid) may constitute from about 0.01 wt. % to about 5 wt. %, in some embodiments from about 0.05 wt. % to about 0.8 wt. %, and in some embodiments, from about 0.1 wt. % to about 0.5 wt. % of the anodizing solution. If desired, blends of acids may also be employed.

A current is passed through the anodizing solution to form the dielectric layer. The value of the formation voltage manages the thickness of the dielectric layer. For example, the power supply may be initially set up at a galvanostatic mode until the required voltage is reached. Thereafter, the power supply may be switched to a potentiostatic mode to ensure that the desired dielectric thickness is formed over the entire surface of the anode. Of course, other known methods may also be employed, such as pulse or step potentiostatic methods. The voltage at which anodic oxidation occurs is typically high to achieve a capacitor capable of operating at a high voltage range. That is, the voltage is typically from about 100 volts to about 300 volts, in some embodiments from about 170 volts to about 280 volts, and in some embodiments, from about 200 volts to about 250 volts. The temperature of the anodizing solution may range from about 10° C. to about 200° C., in some embodiments from about 20° C. to about 150° C., and in some embodiments, from about 30° C. to about 90° C. The resulting dielectric layer may be formed on a surface of the anode and within its pores. When employed, the specific nature of the powder may allow the resulting anode to achieve a high specific charge even at the high formation voltages often employed in the present invention.

II. Capacitor Configuration

The anode of the present invention may generally be employed in any type of capacitor, such as a solid electrolytic capacitor, wet electrolytic capacitor, etc. In one embodiment, for instance, the anode may be employed in a wet electrolytic capacitor that also contains a cathode and a fluidic working electrolyte that is in electrical communication with the anode and the cathode. In this regard, various embodiments of such a wet electrolytic capacitor are described in more detail below.

A. Cathode

The cathode typically contains a metal substrate, which may also optionally serve as a casing for the capacitor. The substrate may be formed from a variety of different metals, such as tantalum, niobium, aluminum, nickel, hafnium, titanium, copper, silver, steel (e.g., stainless), alloys thereof, composites thereof (e.g., metal coated with electrically conductive oxide), and so forth. The geometric configuration of the substrate may generally vary as is well known to those skilled in the art, such as in the form of a foil, sheet, screen, container, can, etc. The metal substrate may form the all or a portion of casing for the capacitor, or it may simply be applied to the casing. Regardless, the substrate may have a variety of shapes, such as generally cylindrical, D-shaped, rectangular, triangular, prismatic, etc. If desired, a surface of the substrate may be roughened to increase its surface area and increase the degree to which a material may be able to adhere thereto. In one embodiment, for example, a surface of the substrate is chemically etched, such as by applying a solution of a corrosive substance (e.g., hydrochloric acid) to the surface. Mechanical roughening may also be employed. For instance, a surface of the substrate may be abrasive blasted by propelling a stream of abrasive media (e.g., sand) against at least a portion of a surface thereof.

A conductive coating may also be disposed on a surface of the metal substrate (e.g., interior surface) to serve as an electrochemically active material for the capacitor. Any number of layers may be employed in the coating. The materials employed in the coating may vary. For example, the conductive coating may contain a noble metal (e.g., ruthenium, rhodium, palladium, silver, osmium, iridium, platinum, gold, etc.), an oxide (e.g., ruthenium oxide), carbonaceous materials, conductive polymers, etc. In one embodiment, for example, the coating may include conductive polymer(s) that are typically π-conjugated and have electrical conductivity after oxidation or reduction. Examples of such Ir-conjugated conductive polymers include, for instance, polyheterocycles (e.g., polypyrroles, polythiophenes, polyanilines, etc.), polyacetylenes, poly-p-phenylenes, polyphenolates, and so forth. Substituted polythiophenes are particularly suitable for use as conductive polymer in that they have particularly good mechanical robustness and electrical performance. In one particular embodiment, the substituted polythiophene has the following general structure:

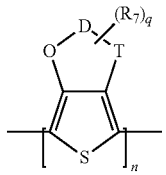

wherein,

T is O or S;

D is an optionally substituted $C_1$ to $C_5$ alkylene radical (e.g., methylene, ethylene, n-propylene, n-butylene, n-pentylene, etc.);

$R_7$ is a linear or branched, optionally substituted $C_1$ to $C_{18}$ alkyl radical (e.g., methyl, ethyl, n- or iso-propyl, n-, iso-, sec- or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadecyl, n-octadecyl, etc.); optionally substituted $C_5$ to $C_{12}$ cycloalkyl radical (e.g., cyclopentyl, cyclohexyl, cycloheptyl, cyclooctyl, cyclononyl cyclodecyl, etc.); optionally substituted $C_6$ to $C_{14}$ aryl radical (e.g., phenyl, naphthyl, etc.); optionally substituted $C_7$ to $C_{18}$ aralkyl radical (e.g., benzyl, o-, m-, p-tolyl, 2,3-, 2,4-, 2,5-, 2-6, 3-4-, 3,5-xylyl, mesityl, etc.); optionally substituted $C_1$ to $C_4$ hydroxyalkyl radical, or hydroxyl radical; and q is an integer from 0 to 8, in some embodiments, from 0 to 2, and in one embodiment, 0; and n is from 2 to 5,000, in some embodiments from 4 to 2,000, and in some embodiments, from 5 to 1,000. Example of substituents for the radicals "D" or "$R_7$" include, for instance, alkyl, cycloalkyl, aryl, aralkyl, alkoxy, halogen, ether, thioether, disulphide, sulfoxide, sulfone, sulfonate, amino, aldehyde, keto, carboxylic acid ester, carboxylic acid, carbonate, carboxylate, cyano, alkylsilane and alkoxysilane groups, carboxylamide groups, and so forth.

Particularly suitable thiophene polymers are those in which "D" is an optionally substituted $C_2$ to $C_3$ alkylene radical. For instance, the polymer may be optionally substituted poly(3,4-ethylenedioxythiophene), which has the following general structure:

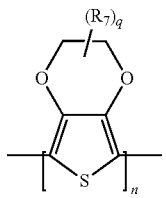

Methods for forming conductive polymers, such as described above, are well known in the art. For instance, U.S. Pat. No. 6,987,663 to Merker, et al. describes various techniques for forming substituted polythiophenes from a monomeric precursor. The monomeric precursor may, for instance, have the following structure:

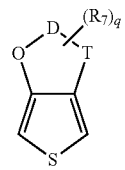

wherein,

T, D, $R_7$, and q are defined above. Particularly suitable thiophene monomers are those in which "D" is an optionally substituted $C_2$ to $C_3$ alkylene radical. For instance, optionally substituted 3,4-alkylenedioxythiophenes may be employed that have the general structure:

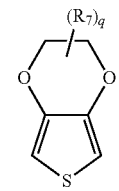

wherein, $R_7$ and q are as defined above. In one particular embodiment, "q" is 0. One commercially suitable example of 3,4-ethylenedioxthiophene is available from Heraeus Clevios under the designation Clevios™ M. Other suitable monomers are also described in U.S. Pat. No. 5,111,327 to Blohm, et al. and U.S. Pat. No. 6,635,729 to Groenendaal, et al. Derivatives of these monomers may also be employed that are, for example, dimers or trimers of the above monomers. Higher molecular derivatives, i.e., tetramers, pentamers, etc. of the monomers are suitable for use in the present invention. The derivatives may be made up of identical or different monomer units and used in pure form and in a mixture with one another and/or with the monomers. Oxidized or reduced forms of these precursors may also be employed.

B. Working Electrolyte

The working electrolyte may be in electrical communication with the cathode and anode. The electrolyte is a fluid that may be impregnated within the anode, or it may be added to the capacitor at a later stage of production. The fluid electrolyte generally uniformly wets the dielectric on the anode. Various suitable electrolytes are described in U.S. Pat. Nos. 5,369,547 and 6,594,140 to Evans, et al. Typically, the electrolyte is ionically conductive in that has an electrical conductivity of from about 0.1 to about 20 Siemens per centimeter ("S/cm"), in some embodiments from about 0.2 to about 15 S/cm, and in some embodiments, from about 0.5 to about 10 S/cm, determined at a temperature of about 23° C. using any known electric conductivity meter (e.g., Oakton Con Series 11). The fluid electrolyte is generally in the form of a liquid, such as a solution (e.g., aqueous or non-aqueous), colloidal suspension, gel, etc. For example, the electrolyte may be an aqueous solution of an acid (e.g., sulfuric acid, phosphoric acid, or nitric acid), base (e.g., potassium hydroxide), or salt (e.g., ammonium salt, such as a nitrate), as well any other suitable electrolyte known in the art, such as a salt dissolved in an organic solvent (e.g., ammonium salt dissolved in a glycol-based solution). Various other electrolytes are described in U.S. Pat. Nos. 5,369,547 and 6,594,140 to Evans, et al.

The desired ionic conductivity may be achieved by selecting ionic compound(s) (e.g., acids, bases, salts, and so forth) within certain concentration ranges. In one particular embodiment, salts of weak organic acids may be effective in achieving the desired conductivity of the electrolyte. The cation of the salt may include monatomic cations, such as alkali metals (e.g., $Li^+$, $Na^+$, $K^+$, $Rb^+$, or $Cs^+$), alkaline earth metals (e.g., $Be^{2+}$, $Mg^{2+}$, $Ca^{2+}$, $Sr^{2+}$ or $Ba^{2+}$), transition metals (e.g., $Ag^+$, $Fe^{2+}$, $Fe^{3+}$, etc.), as well as polyatomic cations, such as $NH_4^+$. The monovalent ammonium ($NH_4^+$), sodium ($K^+$), and lithium ($Li^+$) are particularly suitable cations for use in the present invention. The organic acid used to form the anion of the salt may be "weak" in the sense that it typically has a first acid dissociation constant ($pK_{a1}$) of about 0 to about 11, in some embodiments about 1 to about 10, and in some embodiments, from about 2 to about 10, determined at about 23° C. Any suitable weak organic acids may be used in the present invention, such as carboxylic acids, such as acrylic acid, methacrylic acid, malonic acid, succinic acid, salicylic acid, sulfosalicylic acid, adipic acid, maleic acid, malic acid, oleic acid, gallic acid, tartaric acid (e.g., dextotartaric acid, mesotartaric acid, etc.), citric acid, formic acid, acetic acid, glycolic acid, oxalic acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc.; blends thereof, and so forth. Polyprotic acids (e.g., diprotic, triprotic, etc.) are particularly desirable for use in forming the salt, such as adipic acid ($pK_{a1}$ of 4.43 and $pK_{a2}$ of 5.41), α-tartaric acid ($pK_{a1}$ of 2.98 and $pK_{a2}$ of 4.34), meso-tartaric acid ($pK_{a1}$ of 3.22 and $pK_{a2}$ of 4.82), oxalic acid ($pK_{a1}$ of 1.23 and $pK_{a2}$ of 4.19), lactic acid ($pK_{a1}$ of 3.13, $pK_{a2}$ of 4.76, and $pK_{a3}$ of 6.40), etc.

While the actual amounts may vary depending on the particular salt employed, its solubility in the solvent(s) used in the electrolyte, and the presence of other components, such weak organic acid salts are typically present in the electrolyte in an amount of from about 0.1 to about 25 wt. %, in some embodiments from about 0.2 to about 20 wt. %, in some embodiments from about 0.3 to about 15 wt. %, and in some embodiments, from about 0.5 to about 5 wt. %.

The electrolyte is typically aqueous in that it contains an aqueous solvent, such as water (e.g., deionized water). For example, water (e.g., deionized water) may constitute from about 20 wt. % to about 95 wt. %, in some embodiments from about 30 wt. % to about 90 wt. %, and in some embodiments, from about 40 wt. % to about 85 wt. % of the electrolyte. A secondary solvent may also be employed to form a solvent mixture. Suitable secondary solvents may include, for instance, glycols (e.g., ethylene glycol, propylene glycol, butylene glycol, triethylene glycol, hexylene glycol, polyethylene glycols, ethoxydiglycol, dipropyleneglycol, etc.); glycol ethers (e.g., methyl glycol ether, ethyl glycol ether, isopropyl glycol ether, etc.); alcohols (e.g., methanol, ethanol, n-propanol, iso-propanol, and butanol); ketones (e.g., acetone, methyl ethyl ketone, and methyl isobutyl ketone); esters (e.g., ethyl acetate, butyl acetate, diethylene glycol ether acetate, methoxypropyl acetate, ethylene carbonate, propylene carbonate, etc.); amides (e.g., dimethylformamide, dimethylacetamide, dimethylcaprylic/capric fatty acid amide and N-alkylpyrrolidones); sulfoxides or sulfones (e.g., dimethyl sulfoxide (DMSO) and sulfolane); and so forth. Such solvent mixtures typically contain water in an amount from about 40 wt. % to about 80 wt. %, in some embodiments from about 50 wt. % to about 75 wt. %, and in some embodiments, from about 55 wt. % to about 70 wt. % and secondary solvent(s) in an amount from about 20 wt. % to about 60 wt. %, in some embodiments from about 25 wt. % to about 50 wt. %, and in some embodiments, from about 30 wt. % to about 45 wt. %. The secondary solvent(s) may, for example, constitute from about 5 wt. % to about 45 wt. %, in some embodiments from about 10 wt. % to about 40 wt. %, and in some embodiments, from about 15 wt. % to about 35 wt. % of the electrolyte.

If desired, the electrolyte may be relatively neutral and have a pH of from about 4.5 to about 8.0, in some embodiments from about 5.0 to about 7.5, and in some embodiments, from about 5.5 to about 7.0. One or more pH adjusters (e.g., acids, bases, etc.) may be employed to help achieve the desired pH. In one embodiment, an acid is employed to lower the pH to the desired range. Suitable acids include, for instance, organic acids such as described above; inorganic acids, such as hydrochloric acid, nitric acid, sulfuric acid, phosphoric acid, polyphosphoric acid, boric acid, boronic acid, etc.; and mixtures thereof. Although the total concentration of pH adjusters may vary, they are typically present in an amount of from about 0.01 wt. % to about 10 wt. %, in some embodiments from about 0.05 wt. % to about 5 wt. %, and in some embodiments, from about 0.1 wt. % to about 2 wt. % of the electrolyte.

The electrolyte may also contain other components that help improve the electrical performance of the capacitor. For instance, a depolarizer may be employed in the electrolyte to help inhibit the evolution of hydrogen gas at the cathode of the electrolytic capacitor, which could otherwise cause the capacitor to bulge and eventually fail. When employed, the depolarizer normally constitutes from about 1 to about 500 parts per million ("ppm"), in some embodiments from about 10 to about 200 ppm, and in some embodiments, from about 20 to about 150 ppm of the electrolyte. Suitable depolarizers may include nitroaromatic compounds, such as 2-nitrophenol, 3-nitrophenol, 4-nitrophenol, 2-nitrobenzonic acid, 3-nitrobenzonic acid, 4-nitrobenzonic acid, 2-nitroacetophenone, 3-nitroacetophenone, 4-nitroacetophenone, 2-nitroanisole, 3-nitroanisole, 4-nitroanisole, 2-nitrobenzaldehyde, 3-nitrobenzaldehyde, 4-nitrobenzaldehyde, 2-nitrobenzyl alcohol, 3-nitrobenzyl alcohol, 4-nitrobenzyl alcohol, 2-nitrophthalic acid, 3-nitrophthalic acid, 4-nitrophthalic acid, and so forth. Particularly suitable nitroaromatic depolarizers for use in the present invention are nitrobenzoic acids, anhydrides or salts thereof, substituted with one or more alkyl groups (e.g., methyl, ethyl, propyl, butyl, etc.). Specific examples of such alkyl-substituted nitrobenzoic compounds include, for instance, 2-methyl-3-nitrobenzoic acid; 2-methyl-6-nitrobenzoic acid; 3-methyl-2-nitrobenzoic acid; 3-methyl-4-nitrobenzoic acid; 3-methyl-6-nitrobenzoic acid; 4-methyl-3-nitrobenzoic acid; anhydrides or salts thereof; and so forth.

Figure 4:
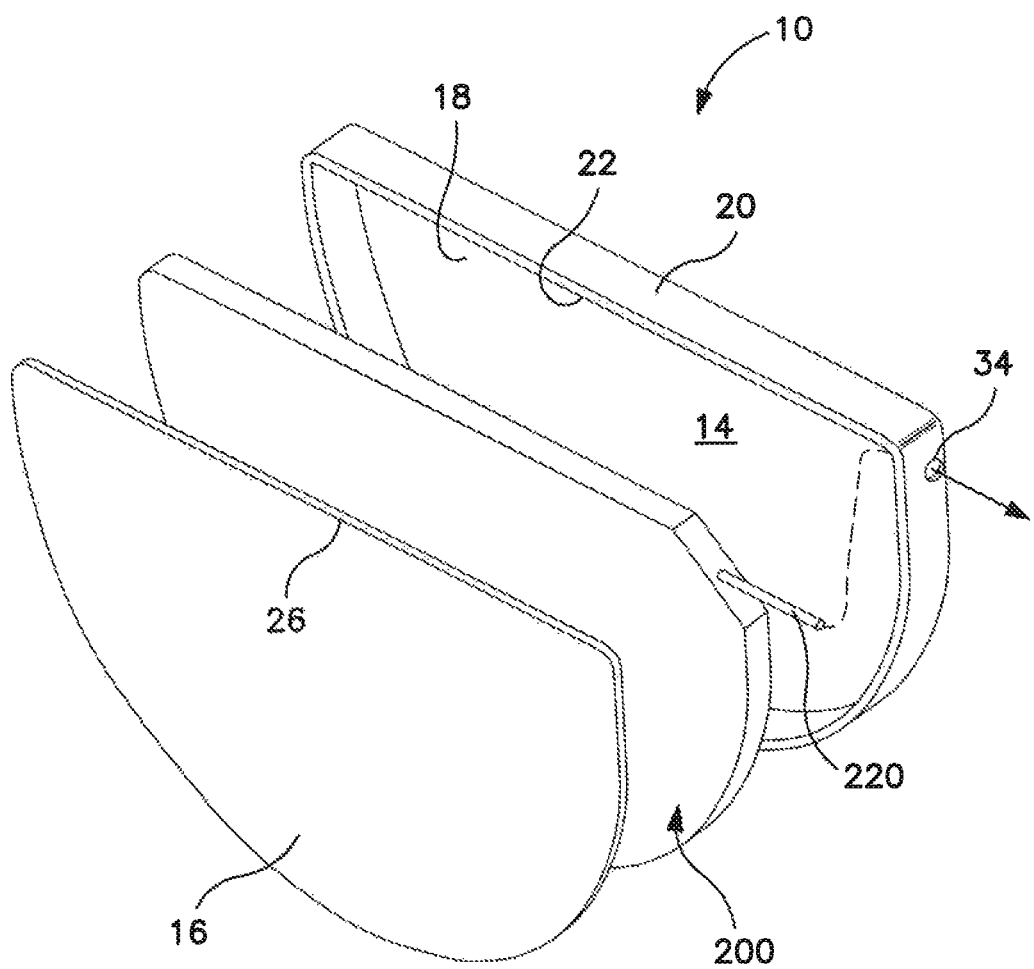
FIG. 4 is a perspective view illustrating the assembly of the anode of FIG. 2 with casing components to form the capacitor shown in FIG. 1.

The particular manner in which the components are incorporated into the capacitor is not critical and may be accomplished using a variety of techniques. In most embodiments, however, the anode is positioned within a casing. Referring to FIGS. 1 and 4, for example, one embodiment of a capacitor 10 is shown that includes the anode 200 shown in FIGS. 2-3. Although only one anode is shown, it should be understood that multiple anodes (e.g., stack) may be employed as is described, for instance, in U.S. Pat. No. 7,483,260 to Ziamiak, et al. In the illustrated embodiment, the anode 200 may be positioned within a casing 12 made of a first casing member 14 and a second casing member 16.

The first casing member 14 has a face wall 18 joined to a surrounding sidewall 20, which extends to an edge 22. The second casing member 16 may likewise contain a second face wall 24 having a surrounding edge 26. In the illustrated embodiment, the second casing member 16 is thus in the form of a plate that serves as a lid for the casing 10. The casing members 14 and 16 may be hermetically sealed together by welding (e.g., laser welding) the edges 22 and 26 where they contact each other. The casing members 14 and/or 16 may be analogous to the metal substrate described above such that a conductive polymer coating (not shown) may be deposited on the interior surface thereof. Alternatively, a separate metal substrate may be located adjacent to the casing member 14 and/or 16 and applied with the conductive polymer coating.

Although not shown, one or more separators may be employed between the anode and cathode (e.g., between the anode 200 and the first casing member 14, between the anode 200 and the second casing member 16, or between the anode and both casing members) that help insulate the anode and conductive polymer-coated cathode from each other. Examples of suitable materials for this purpose include, for instance, porous polymer materials (e.g., polypropylene, polyethylene, etc.), porous inorganic materials (e.g., fiberglass mats, porous glass paper, etc.), ion exchange resin materials, etc. Particular examples include ionic perfluoronated sulfonic acid polymer membranes (e.g., Nafion™ from the E.I. DuPont de Nemeours & Co.), sulphonated fluorocarbon polymer membranes, polybenzimidazole (PBI) membranes, and polyether ether ketone (PEEK) membranes. Although preventing direct contact between the anode and cathode, the separator permits ionic current flow of the electrolyte to the electrodes.

A feedthrough 30 (FIG. 1) may also be employed that electrically insulates the anode wire 200 from the casing 12. The feedthrough 30 extends from within the casing 12 to the outside thereof. A hole 34 may be provided in the surrounding sidewall 20 of the casing member 14 into which the feedthrough 30. The feedthrough 30 may, for example, be a glass-to-metal seal ("GTMS") that contains a ferrule (not shown) with an internal cylindrical bore of a constant inside diameter. An insulative glass can thus provide a hermetic seal between the bore and the anode wire 200 passing therethrough. After assembly and sealing (e.g., welding), the electrolyte may optionally be introduced into the casing through a fill-port. Filling may be accomplished by placing the capacitor in a vacuum chamber so that the fill-port extends into a reservoir of the electrolyte. When the chamber is evacuated, pressure is reduced inside the capacitor. When the vacuum is released, pressure inside the capacitor re-equilibrates, and the electrolyte is drawn through the fill-port into the capacitor.

Regardless of its particular configuration, the capacitor of the present invention may exhibit excellent electrical properties. For example, the capacitor may exhibit a high volumetric efficiency, such as from about 50,000 µF*V/cm³ to about 300,000 µF*V/cm³, in some embodiments from about 60,000 µF*V/cm³ to about 200,000 µF*V/cm³, and in some embodiments, from about 80,000 µF*V/cm³ to about 150,000 µF*V/cm³, determined at a frequency of 120 Hz and at room temperature (e.g., 25° C.). Volumetric efficiency is determined by multiplying the formation voltage of a part by its capacitance, and then dividing by the product by the volume of the part. For example, a formation voltage may be 175 volts for a part having a capacitance of 520 µF, which results in a product of 91,000 µF*V. If the part occupies a volume of about 0.8 cm³, this results in a volumetric efficiency of about 113,750 µF*V/cm³.

The capacitor may also exhibit a high energy density that enables it suitable for use in high pulse applications. Energy density is generally determined according to the equation $E=1/2*CV^2$, where C is the capacitance in farads (F) and V is the working voltage of capacitor in volts (V). The capacitance may, for instance, be measured using a capacitance meter (e.g., Keithley 3330 Precision LCZ meter with Kelvin Leads, 2 volts bias and 1 volt signal) at operating frequencies of from 10 to 120 Hz (e.g., 120 Hz) and a temperature of 25° C. For example, the capacitor may exhibit an energy density of about 2.0 joules per cubic centimeter (J/cm³) or more, in some embodiments about 3.0 J/cm³, in some embodiments from about 3.5 J/cm³ to about 10.0 J/cm³, and in some embodiments, from about 4.0 to about 8.0 J/cm³. The capacitance may likewise be about 1 milliFarad per square centimeter ("mF/cm²") or more, in some embodiments about 2 mF/cm² or more, in some embodiments from about 5 to about 50 mF/cm², and in some embodiments, from about 8 to about 20 mF/cm² The capacitor may also exhibit a relatively high "breakdown voltage" (voltage at which the capacitor fails), such as about 180 volts or more, in some embodiments about 200 volts or more, and in some embodiments, from about 210 volts to about 260 volts.

The equivalent series resistance ("ESR")—the extent that the capacitor acts like a resistor when charging and discharging in an electronic circuit—may also be less than about 15,000 milliohms, in some embodiments less than about 10,000 milliohms, in some embodiments less than about 5,000 milliohms, and in some embodiments, from about 1 to about 4,500 milliohms, measured with a 2-volt bias and 1-volt signal at a frequency of 120 Hz. In addition, the leakage current, which generally refers to the current flowing from one conductor to an adjacent conductor through an insulator, can be maintained at relatively low levels. For example, the numerical value of the normalized leakage current of a capacitor of the present invention is, in some embodiments, less than about 1 µA/µF*V, in some embodiments less than about 0.5 µA/µF*V, and in some embodiments, less than about 0.1 µA/µF*V, where µA is microamps and µF*V is the product of the capacitance and the rated voltage. Leakage current may be measured using a leakage test meter (e.g., MC 190 Leakage test, Mantracourt Electronics LTD, UK) at a temperature of 25° C. and at a certain rated voltage after a charging time of from about 60 to about 300 seconds. Such ESR and normalized leakage current values may even be maintained after aging for a substantial amount of time at high temperatures. For example, the values may be maintained for about 100 hours or more, in some embodiments from about 300 hours to about 2500 hours, and in some embodiments, from about 400 hours to about 1500 hours (e.g., 500 hours, 600 hours, 700 hours, 800 hours, 900 hours, 1000 hours, 1100 hours, or 1200 hours) at temperatures ranging from about 100° C. to about 250° C., and, in some embodiments from about 100° C. to about 200° C. (e.g., 100° C., 125° C., 150° C., 175° C., or 200° C.).

The electrolytic capacitor of the present invention may be used in various applications, including but not limited to implantable medical devices, such as implantable defibrillators, pacemakers, cardioverters, neural stimulators, drug administering devices, etc. In one embodiment, for example, the capacitor may be employed in an implantable medical device configured to provide a therapeutic high voltage (e.g., between approximately 500 volts and approximately 850 volts, or, desirably, between approximately 600 Volts and approximately 900 volts) treatment for a patient. The device may contain a container or housing that is hermetically sealed and biologically inert. One or more leads are electrically coupled between the device and the patient's heart via a vein. Cardiac electrodes are provided to sense cardiac activity and/or provide a voltage to the heart. At least a portion of the leads (e.g., an end portion of the leads) may be provided adjacent or in contact with one or more of a ventricle and an atrium of the heart. The device may also contain a capacitor bank that typically contains two or more capacitors connected in series and coupled to a battery that is internal or external to the device and supplies energy to the capacitor bank. Due in part to high conductivity, the capacitor of the present invention can achieve excellent electrical properties and thus be suitable for use in the capacitor bank of the implantable medical device.

The present invention may be better understood by reference to the following example.

Test Procedures

Capacitance, equivalent series resistance, and leakage current may be tested in a neutral electrolyte at a temperature of 37° C.±0.5° C. in a manner as described below.

Capacitance ("CAP")

Capacitance may be measured using a Keithley 3330 Precision LCZ meter with Kelvin Leads with 2.2 volt DC bias and a 0.5 volt peak to peak sinusoidal signal. The operating frequency may be 120 Hz.

Equivalent Series Resistance ("ESR")

Equivalence series resistance may be measured using a Keithley 3330 Precision LCZ meter with Kelvin Leads 2.2 volt DC bias and a 0.5 volt peak to peak sinusoidal signal. The operating frequency may be 120 Hz.

Leakage Current ("DCL")

Leakage current may be determined by charging to 250V for 300 seconds without any resistor in series.

EXAMPLE

The ability to form a capacitor in accordance with the present invention was demonstrated. Samples of a nodular tantalum powder (with 4% stearic acid lubricant) were pressed together with a 0.50-mm tantalum wire using a two-sided press. In one set of samples ("Sample 1"), the wire was positioned so that multiple layers were defined in the anode (the thickness of one layer was 1.25 mm and the thickness of the other layer was 0.75 mm). In another set of samples ("Sample 2"), the anode wire was simply positioned in the middle of the anode. In each case, the resulting press density was 5.3 g/cm³. Once pressed, the samples were delubricated and then vacuum-sintered at 1400° C. for 20 minutes in a hanging crucible. Upon sintering, the pellets were anodized in a solution containing 50% glycol/water with phosphoric acid at a temperature of 85° C. and a conductivity of 1 mS/cm. The formation current density was 45 mA/g for each sample and the voltage was 220 volts. The resulting anodes had a D-shape in which the length was about 32 millimeters, the width was about 23 millimeters, and the thickness was about 2 millimeters. Once formed, the anodes were joined together with two cathodes prepared from Pd/PEDT coated titanium sheets (0.1 mm thick) separated with two plastic meshes (0.2 mm thick).

Multiple parts (32) of capacitors were made in the manner described above and tested for CAP, ESR and DCL in an aqueous neutral electrolyte. The percentage of cracks around the anode lead wire were also determined. The results are shown in the table below.

|  | % Cracks Around Wire | CAP [µF] | ESR [Ohm] | DCL [µA] |
| --- | --- | --- | --- | --- |
| Sample 1 | 5 | 466 | 1.8 | 216 |
| Sample 2 | 60 | 458 | 1.9 | 2174 |

As shown, the capacitors with a multi-layered anode (Sample 1) had less mechanical fails around the wire and thus improved electrical properties.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A wet electrolytic capacitor comprising:
an anode that comprises a sintered porous pellet and a dielectric layer formed on the pellet, wherein the pellet contains a first layer positioned adjacent to a second layer, wherein the first layer has a thickness greater than that of the second layer, wherein a leadwire is embedded in the first layer of the pellet that extends therefrom in a longitudinal direction and has a thickness of about 0.1 millimeter or more, wherein the first layer and the second layer are contiguous along a length of the anode;
a cathode that comprises a metal substrate coated with a conductive coating; and
a fluidic working electrolyte in communication with the anode and the cathode.

2. The wet electrolytic capacitor of claim 1, wherein the ratio of the thickness of the first layer to the thickness of the second layer is from about 1.0 to about 5.0.

3. The wet electrolytic capacitor of claim 1, wherein thickness of the first layer is from about 0.2 to about 10 millimeters.

4. The wet electrolytic capacitor of claim 1, wherein the thickness of the second layer is from about 0.1 to about 5 millimeters.

5. The wet electrolytic capacitor of claim 1, wherein the anode is planar.

6. The wet electrolytic capacitor of claim 1, wherein the metal substrate includes titanium or stainless steel.

7. The wet electrolytic capacitor of claim 1, wherein the conductive coating includes a substituted polythiophene.

8. The wet electrolytic capacitor of claim 1, wherein the electrolyte has a pH of from about 5.0 to about 7.5.

9. The wet electrolytic capacitor of claim 1, wherein a separator is positioned between the anode and cathode.

10. The wet electrolytic capacitor of claim 1, wherein the capacitor contains a casing that contains a first casing member and a second casing member between which the anode and the fluid working electrolyte are disposed, wherein the metal substrate forms at least a portion of the first casing member, the second casing member, or both.

11. The wet electrolytic capacitor of claim 10, wherein the first casing member contains a face wall and a surrounding sidewall that extends to an edge, and further wherein the second casing member is in the form of a lid that is sealed to the edge of the sidewall.

12. An implantable medical device comprising the capacitor of claim 1.

13. The wet electrolytic capacitor of claim 1, wherein the anode is formed by a method that comprises:
   loading a first valve metal powder into a first die cavity of a press mold, wherein an anode leadwire is embedded within the first valve metal powder;
   loading a second valve metal powder to a second die cavity of the press mold;
   forming a pellet by compressing the first valve metal powder with a first punch and compressing the second valve metal powder with a second punch;
   sintering the pellet; and
   anodically oxidizing the sintered pellet o form a dielectric layer.

14. The method of claim 13, wherein the powders are compressed in a direction that is substantially perpendicular to a longitudinal axis of the leadwire.

15. The method of claim 13, wherein the first and second valve metal powders include tantalum particles.

16. The wet electrolytic capacitor of claim 1, wherein the first layer and the second layer of the pellet are each formed from a valve metal powder.

17. The wet electrolytic capacitor of claim 16, wherein the valve metal powder includes tantalum particles.

18. The wet electrolytic capacitor of claim 1, wherein the anode has a D-shape.

* * * * *